US007300786B2

(12) United States Patent
Klyachko et al.

(10) Patent No.: US 7,300,786 B2
(45) Date of Patent: Nov. 27, 2007

(54) BACTERIA OF THE ENTEROBACTERIACEAE FAMILY HAVING ENHANCED TRANSALDOLASE ACTIVITY

(75) Inventors: Elena Vitalievna Klyachko, Moscow (RU); Rustam Saidovich Shakulov, Moscow (RU); Yuri Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/892,113

(22) Filed: Jul. 16, 2004

(65) Prior Publication Data

US 2005/0054061 A1 Mar. 10, 2005

(30) Foreign Application Priority Data

Jul. 16, 2003 (RU) .............. 2003121600

(51) Int. Cl.
*C12N 1/20* (2006.01)
*C12N 9/10* (2006.01)

(52) U.S. Cl. .............. 435/252.3; 435/252.33; 435/193; 536/23.2

(58) Field of Classification Search ............ 435/252.3, 435/252.33, 23.1, 193; 536/23.2
See application file for complete search history.

(56) References Cited

U.S. PATENT DOCUMENTS

| | | | | |
|---|---|---|---|---|
| 4,278,765 | A | 7/1981 | Debabov et al. | 435/172 |
| 5,168,056 | A | 12/1992 | Frost | |
| 5,196,326 | A | 3/1993 | Kuronuma et al. | |
| 5,661,012 | A | 8/1997 | Sano et al. | 435/115 |
| 6,040,160 | A | 3/2000 | Kojima et al. | 435/115 |
| 6,297,031 | B1 | 10/2001 | Debabov et al. | 435/115 |
| 6,316,232 | B1 | 11/2001 | Sprenger et al. | 435/156 |
| 6,653,111 | B2 | 11/2003 | Debabov et al. | 435/115 |
| 2001/0049126 | A1 | 12/2001 | Livshits et al. | 435/106 |
| 2004/0038380 | A1 | 2/2004 | Debabov et al. | 435/115 |
| 2004/0132165 | A1 | 7/2004 | Akhverdian et al. | 435/252 |
| 2004/0229320 | A1 | 11/2004 | Stoynova et al. | 435/106 |
| 2004/0229321 | A1 | 11/2004 | Savrasova et al. | 435/106 |

FOREIGN PATENT DOCUMENTS

| | | |
|---|---|---|
| EP | 1016710 | 7/2000 |
| EP | 1085087 | 3/2001 |
| EP | 1 225 218 | 7/2002 |
| EP | 1225218 | 7/2002 |
| JP | 56-018596 A | 2/1981 |
| RU | 2119536 | 9/1998 |
| WO | 03/008605 | 1/2003 |
| WO | WO 03/008600 A2 | 1/2003 |
| WO | WO 03/008611 A2 | 1/2003 |

OTHER PUBLICATIONS

Lohkamp et al., "The Structure of *Escherichia coli* ATP-phosphoriboxytransferase: Identification of Substrate Binding Sites and Mode of AMP Inhibition" 2004, Journal of Molecular Biology, vol. 335, pp. 131-144.*
Sprenger G. A., et al., "Transaldolase B of *Escherichia coli* K-12: Cloning of Its Gene, *talB*, and Characterization of the Enzyme from Recombinant Strains", Journal of Bacteriology, vol. 177, No. 20, p. 5930-5936, (1995).
Copy of International Preliminary Report on Patentability for PCT Patent App. No. PCT/JP2004/010215 (May 26, 2006).
Kwon, J., et al., "Cloning of the histidine biosynthetic genes from *Corynebacterium glutamicum*: Organization and analysis of the *hisG* and *hisE* genes," Can. J. Microbiol. 2000:46(9):848-855.
Copy of International Search Report for PCT Appl. No. PCT/JP2004/010215 (Aug. 31, 2004).
Alifano, P., et al., "Histidine Biosynthetic Pathway and Genes: Structure, Regulation, and Evolution, " Microbiol. Rev. 1996;60(1):44-69.
Fani, R., et al., "Evolution of the Structure and Chromosomal Distribution of Histidine Biosynthetic Genes, " Orgins of Life and Evolution of the Biosphere 1998;28:555-570.
Ikeda, M., et al., "Cloning of the transketolase gene and the effect of its dosage on aromatic amino acid production in *Corynebacterium glutamicum*, " Appl. Microbiol. Biotechnol. 1999;51(2):201-206.
Ikeda, M., et al., "Hyperproduction of Tryptophan by *Corynebacterium glutamicum* with the Modified Pentose Phosphate Pathway, " Appl. Environmen. Microbiol. 1999;65(6):2497-2505.
Krömer, J. O., et al., "In-Depth Profiling of Lysine-Producing *Corynebacterium glutamicum* by Combined Analysis of the Transcriptome, Metabolome, and Fluxome, " J. Bacteriol. 2004;186(6):1769-1784.
Lu, J-L., et al., "Metabolic Engineering and Control Analysis for Production of Aromatics: Role of Transaldolase, " Biotechnol. Bioeng. 1997;53:132-138.
Copy of SEARCH REPORT for EP Patent App. No. 04747680.9 (Apr. 11, 2007).

* cited by examiner

*Primary Examiner*—Tekchand Saidha
(74) *Attorney, Agent, or Firm*—Shelly Guest Cermak; Cermak Kenealy & Vaidya, LLP

(57) ABSTRACT

A method is provided for producing L-histidine using bacterium of the Enterobacteriaceae family, wherein the L-amino acid productivity of said bacterium is enhanced by enhancing an activity of the transaldolase encoded by the talb gene.

14 Claims, No Drawings

SEQUENCE LISTING

<160> NUMBER OF SEQ ID NOS: 5

<210> SEQ ID NO 1
<211> LENGTH: 954
<212> TYPE: DNA
<213> ORGANISM: Escherichia coli
<220> FEATURE:
<221> NAME/KEY: CDS
<222> LOCATION: (1)..(954)

<400> SEQUENCE: 1

```
atg acg gac aaa ttg acc tcc ctt cgt cag tac acc acc gta gtg gcc    48
Met Thr Asp Lys Leu Thr Ser Leu Arg Gln Tyr Thr Thr Val Val Ala
 1               5                  10                  15 gac act ggg gac atc gcg gca atg aag ctg tat caa ccg cag gat gcc    96
Asp Thr Gly Asp Ile Ala Ala Met Lys Leu Tyr Gln Pro Gln Asp Ala
             20                  25                  30 aca acc aac cct tct ctc att ctt aac gca gcg cag att ccg gaa tac   144
Thr Thr Asn Pro Ser Leu Ile Leu Asn Ala Ala Gln Ile Pro Glu Tyr
         35                  40                  45 cgt aag ttg att gat gat gct gtc gcc tgg gcg aaa cag cag agc aac   192
Arg Lys Leu Ile Asp Asp Ala Val Ala Trp Ala Lys Gln Gln Ser Asn
     50                  55                  60 gat cgc gcg cag cag atc gtg gac gcg acc gac aaa ctg gca gta aat   240
Asp Arg Ala Gln Gln Ile Val Asp Ala Thr Asp Lys Leu Ala Val Asn
 65                  70                  75                  80 att ggt ctg gaa atc ctg aaa ctg gtt ccg ggc cgt atc tca act gaa   288
Ile Gly Leu Glu Ile Leu Lys Leu Val Pro Gly Arg Ile Ser Thr Glu
                 85                  90                  95 gtt gat gcg cgt ctt tcc tat gac acc gaa gcg tca att gcg aaa gca   336
Val Asp Ala Arg Leu Ser Tyr Asp Thr Glu Ala Ser Ile Ala Lys Ala
            100                 105                 110 aaa cgc ctg atc aaa ctc tac aac gat gct ggt att agc aac gat cgt   384
Lys Arg Leu Ile Lys Leu Tyr Asn Asp Ala Gly Ile Ser Asn Asp Arg
        115                 120                 125 att ctg atc aaa ctg gct tct acc tgg cag ggt atc cgt gct gca gaa   432
Ile Leu Ile Lys Leu Ala Ser Thr Trp Gln Gly Ile Arg Ala Ala Glu
    130                 135                 140
```

```
cag ctg gaa aaa gaa ggc atc aac tgt aac ctg acc ctg ctg ttc tcc    480
Gln Leu Glu Lys Glu Gly Ile Asn Cys Asn Leu Thr Leu Leu Phe Ser
145                 150                 155                 160 ttc gct cag gct cgt gct tgt gcg gaa gcg ggc gtg ttc ctg atc tcg    528
Phe Ala Gln Ala Arg Ala Cys Ala Glu Ala Gly Val Phe Leu Ile Ser
                165                 170                 175 ccg ttt gtt ggc cgt att ctt gac tgg tac aaa gcg aat acc gat aag    576
Pro Phe Val Gly Arg Ile Leu Asp Trp Tyr Lys Ala Asn Thr Asp Lys
            180                 185                 190 aaa gag tac gct ccg gca gaa gat ccg ggc gtg gtt tct gta tct gaa    624
Lys Glu Tyr Ala Pro Ala Glu Asp Pro Gly Val Val Ser Val Ser Glu
        195                 200                 205 atc tac cag tac tac aaa gag cac ggt tat gaa acc gtg gtt atg ggc    672
Ile Tyr Gln Tyr Tyr Lys Glu His Gly Tyr Glu Thr Val Val Met Gly
    210                 215                 220 gca agc ttc cgt aac atc ggc gaa att ctg gaa ctg gca ggc tgc gac    720
Ala Ser Phe Arg Asn Ile Gly Glu Ile Leu Glu Leu Ala Gly Cys Asp
225                 230                 235                 240 cgt ctg acc atc gca ccg gca ctg ctg aaa gag ctg gcg gag agc gaa    768
Arg Leu Thr Ile Ala Pro Ala Leu Leu Lys Glu Leu Ala Glu Ser Glu
                245                 250                 255 ggg gct atc gaa cgt aaa ctg tct tac acc ggc gaa gtg aaa gcg cgt    816
Gly Ala Ile Glu Arg Lys Leu Ser Tyr Thr Gly Glu Val Lys Ala Arg
            260                 265                 270 ccg gcg cgt atc act gag tcc gag ttc ctg tgg cag cac aac cag gat    864
Pro Ala Arg Ile Thr Glu Ser Glu Phe Leu Trp Gln His Asn Gln Asp
        275                 280                 285 cca atg gca gta gat aaa ctg gcg gaa ggt atc cgt aag ttt gct att    912
Pro Met Ala Val Asp Lys Leu Ala Glu Gly Ile Arg Lys Phe Ala Ile
    290                 295                 300 gac cag gaa aaa ctg gaa aaa atg atc ggc gat ctg ctg taa            954
Asp Gln Glu Lys Leu Glu Lys Met Ile Gly Asp Leu Leu
305                 310                 315

<210> SEQ ID NO 2
<211> LENGTH: 317
<212> TYPE: PRT
<213> ORGANISM: Escherichia coli

<400> SEQUENCE: 2

Met Thr Asp Lys Leu Thr Ser Leu Arg Gln Tyr Thr Thr Val Val Ala
 1               5                  10                  15

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Asn
    50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
    130                 135                 140
```

-continued

```
Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
    210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
            260                 265                 270

Pro Ala Arg Ile Thr Glu Ser Glu Phe Leu Trp Gln His Asn Gln Asp
        275                 280                 285

Pro Met Ala Val Asp Lys Leu Ala Glu Gly Ile Arg Lys Phe Ala Ile
    290                 295                 300

Asp Gln Glu Lys Leu Glu Lys Met Ile Gly Asp Leu Leu
305                 310                 315

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 3
ctcagatctg acgttgcgtc gtgatatca                                              29

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 4
ctctctagac cgtttaaaca gtctcgttaa a                                           31

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
cgcgcttcaa atgaaacaga t                                                     21
```

BACTERIA OF THE ENTEROBACTERIACEAE FAMILY HAVING ENHANCED TRANSALDOLASE ACTIVITY

BACKGROUND OF THE INVENTION

1. Field of the Invention

The present invention relates to biotechnology, and specifically to a method for producing an L-amino acid such as L-histidine, by fermentation. The present invention further relates to a gene derived from an *Escherichia coli* bacterium. The gene is useful for improving production of L-histidine.

2. Description of the Related Art

Conventionally, L-amino acids have been industrially produced by fermentation utilizing strains of microorganisms obtained from natural sources, or mutants of the same modified to enhance L-amino acid productivity.

Many techniques have been reported regarding enhancement of L-amino acid production, for example, by transformation of microorganism by recombinant DNA (see, for example, U.S. Pat. No. 4,278,765). These techniques are based on increasing of activities of enzymes involved in amino acid biosynthesis and/or desensitizing target enzymes from feedback inhibition by the produced L-amino acid (see, for example, Japanese Laid-open application No 56-18596 (1981), WO 95/16042 or U.S. Pat. Nos. 5,661,012 and 6,040,160).

The talB gene encodes transaldolase (also known as TAL, or D-sedoheptulose-7-phosphate:D-glyceraldehyde-3-phosphate dihydroxyacetonetransferase) [EC 2.2.1.2], an enzyme of the non-oxidative pentose phosphate cycle (Sprenger G. A. et al, J. Bacteriol., 1995, October 177:20, 5930-6). Transaldolase is a key enzyme in biosynthesis of ribose-5-phosphate from glycolysis products. The enzyme catalyzes the reversible transfer of a dihydroacetone moiety derived from fructose-6-phosphate to erythrose-4-phosphate, forming sedoheptulose-7-phosphate and releasing glyceraldehyde-3-phosphate. Then sedoheptulose-7-phosphate and glyceraldehydes-3-phosphate are converted to two molecules of pentose-5-phosphate by the activity of transketolase.

Previously it has been reported that increasing the activity of transaldolase is useful for microbial production of substances from aromatic metabolism, in particular aromatic amino acids such as L-phenylalanine (U.S. Pat. No. 6,316,232).

Recently, it has been suggested based solely on theory that preparation of L-threonine by fermentation of microorganisms of the Enterobacteriaceae family, whereby one or more genes from a large group of genes, including the talB gene, are attenuated, in particular eliminated, can be accomplished. No experimental data, however, proving this theory was presented (WO03008600A2). At the same time, and in direct contradiction, preparation of L-threonine by fermentation of microorganisms of the Enterobacteriaceae family in which expression of at least talB gene is enhanced, in particular over-expressed, was disclosed WO03/008611A2).

There have been no reports to date, however, describing amplification of the talB gene for the purpose of enhancing L-histidine production using strains of the Enterobacteriaceae family.

SUMMARY OF THE INVENTION

An object of the present invention is to develop an L-histidine-producing microorganism strain which has enhanced productivity of L-histidine. It is a further object of the invention to provide a method for producing L-histidine using such a strain.

It is a further object of the present invention to provide an L-histidine-producing bacterium of the Enterobacteriaceae family, wherein the bacterium has been modified to enhance an activity of transaldolase.

It is a further object of the present invention to provide the bacterium as described above, wherein the bacterium belongs to the genus *Escherichia*.

It is a further object of the present invention to provide the bacterium as described above, wherein the activity of transaldolase is enhanced by increasing the expression amount of a transaldolase gene.

It is a further object of the present invention to provide the bacterium as described above, wherein the activity of transaldolase is increased by increasing the copy number of the transaldolase gene or by modifying an expression control sequence of the gene so that the expression of the gene is enhanced.

It is a further object of the present invention to provide the bacterium as described above, wherein the copy number is increased by transformation of the bacterium with multi-copy vector harboring transaldolase gene.

It is a further object of the present invention to provide the bacterium as described above, the transaldolase gene is originated from a bacterium belonging to the genus *Escherichia*.

It is a further object of the present invention to provide the bacterium as described above, wherein the transaldolase gene encodes the following protein (A) or (B):

(A) a protein which comprises the amino acid sequence shown in SEQ ID NO: 2;

(B) a protein which comprises an amino acid sequence including deletion, substitution, insertion or addition of one or several amino acids in the amino acid sequence shown in SEQ ID NO: 2, and which has an activity of transaldolase.

Hereinafter, the proteins as defined in the above (A) or (B) are referred to as "proteins of the present invention".

It is a further object of the present invention to provide the bacterium as described above, wherein the transaldolase gene comprises the following DNA (a) or (b):

(a) a DNA which comprises a nucleotide sequence of the nucleotides 1 to 954 in SEQ ID NO: 1; or (b) a DNA which is hybridizable with a nucleotide sequence of the nucleotides 1-954 in SEQ ID NO: 1 or a probe which can be prepared from the nucleotide sequence under the stringent conditions, and encodes a protein having an activity of transaldolase.

It is a further object of the present invention to provide the bacterium as described above, wherein the stringent conditions are conditions in which washing is performed at 60° C., and at a salt concentration corresponding to 1×SSC and 0.1% SDS.

It is a still further object of the present invention to provide a method for producing L-histidine, which comprises cultivating the bacterium as described above in a culture medium to produce and accumulate L-histidine in the culture medium, and collecting the L-histidine from the culture medium.

It is even a further object of the present invention to provide the method as described above, wherein the bacterium has enhanced expression of genes for histidine biosynthesis.

DETAILED DESCRIPTION OF THE INVENTION

The aforementioned objects were achieved by identifying the talB gene encoding transaldolase (TAL, D-sedoheptulose-7-phosphate:D-glyceraldehyde-3-phosphate dihydroxyacetonetransferase [EC 2.2.1.2]), which is not involved in biosynthetic pathway of the target L-amino acid, but which can enhance L-histidine production when additional copies are introduced into the cells of the respective producing strain. Thus, the present invention has been completed.

The present invention will be explained in detail below.

The bacterium of the present invention is an L-histidine-producing bacterium of the Enterobacteriaceae family, wherein L-histidine production by the bacterium is enhanced by enhancing an activity of the protein of the present invention in the bacterium. Specifically, the bacterium of the present invention is an L-histidine-producing bacterium belonging to the genus *Escherichia*, wherein L-histidine production by the bacterium is enhanced by enhancing an activity of the protein of the present invention, namely transaldolase, in the bacterium. More specifically, the bacterium of present invention harbors chromosomal or plasmid DNA which includes the talB gene, and has enhanced ability to produce L-histidine by virtue of overexpression of the talB gene.

"L-histidine-producing bacterium" means a bacterium, which has an ability to produce and cause accumulation of L-histidine in a medium, when the bacterium of the present invention is cultured in the medium. The L-histidine-producing ability may be imparted or enhanced by breeding. The term "L-histidine-producing bacterium" as used herein may also mean a bacterium which is able to produce and cause accumulation of L-histidine in a culture medium in an amount larger than a wild-type or parental strain, and preferably means the microorganism which is able to produce and cause accumulation in a medium of an amount of not less than 0.5 g/L, more preferably not less than 1.0 g/L of L-histidine.

The Enterobacteriaceae family of bacteria includes bacteria belonging to the genera *Escherichia*, *Erwinia*, *Providencia* and *Serratia*. The genus *Escherichia* is preferred.

The phrase "a bacterium belonging to the genus *Escherichia*" means that the bacterium which is classified as the genus *Escherichia* according to the classification known to a person skilled in the art of microbiology. A microorganism belonging to the genus *Escherichia* as used in the present invention includes, but is not limited to *Escherichia coli* (*E. coli*).

The phrase "activity of transaldolase" means an activity to catalyze the reaction of reversible transfer of a dihydroacetone moiety derived from fructose-6-phosphate to erythrose-4-phosphate, forming sedoheptulose-7-phosphate and releasing glyceraldehyde-3-phosphate. The activity of the transaldolase may be measured by the method described by, for example, G A. Sprenger, U. Schorken, G. Sprenger & H. Sahm (Transaldolase B of *Escherichia coli* K-12: cloning of its gene, talB, and characterization of the enzyme from recombinant strains. J. Bacteriol., 1995, 177:20:5930-6).

The phrase "modified to enhance an activity of transaldolase" means that the bacterium has been modified so that the activity per cell is higher than that of a non-modified strain, for example, a wild-type strain. For example, cells in which the number of transaldolase molecules per cell increases, cells in which specific activity per transaldolase molecule increases, and so forth are encompassed. Furthermore, the wild-type strain that can serve as an object for comparison includes, for example, the *Escherichia coli* K-12. As a result of the enhancement of intracellular activity of transaldolase, L-histidine accumulation in a medium is increased.

Enhancement of transaldolase activity in a bacterial cell can be achieved by enhancement of expression of a gene encoding transaldolase. Genes encoding transaldolase derived from bacteria of the Enterobacteriaceae family and/or genes derived from other bacteria, such as coryneform bacteria, can be used. Genes derived from bacteria belonging to the genus *Escherichia* are preferred.

As the gene encoding transaldolase of *Escherichia coli* (EC number 2.2.1.2), talB gene has already been reported (nucleotide numbers 8238 to 9191 in the sequence of GenBank accession NC_000913.1, gi:16128002). Therefore, the talB gene can be obtained by PCR (polymerase chain reaction; refer to White, T. J. et al., Trends Genet., 5, 185 (1989)) utilizing primers based on the nucleotide sequence of the gene. Genes encoding transaldolase of other microorganisms can be obtained in a similar manner.

An Example of the talB gene derived from *Escherichia coli* includes a DNA which encodes the following protein (A) or (B):

(A) a protein, which comprises the amino acid sequence shown in SEQ ID NO:2;

(B) a protein which comprises the amino acid sequence including deletion, substitution, insertion or addition of one or several amino acids in the amino acid sequence shown in SEQ ID NO:2, and which has an activity of transaldolase.

The DNA encoding proteins of the present invention includes a DNA encoding the protein possibly having deletions, substitutions, insertions or additions of one or several amino acids in one or more positions on the protein (A) as long as they do not result in loss of the protein's activity. The number of "several" amino acids differs depending on the position of amino acid residues in the three-dimensional structure of the protein and the type of the amino acids. However, it preferably means between 2 to 30, more preferably between 2 to 20, and most preferably between 2 to 10 for the protein (A). This is because of the following reason. Some amino acids have high homology to one another and the difference in such an amino acid does not greatly affect the three dimensional structure of the protein and its activity. Therefore, the protein (B) may be one which has homology of not less than 30 to 50%, preferably 50 to 70%, more preferably 70 to 90%, more preferably not less than 90%, and most preferably not less than 95% with respect to the entire amino acid sequence of transaldolase, and which has the activity of transaldolase.

Homologous proteins of transaldolase which are able to retain the transaldolase activity may be determined by the person of ordinary skill in the art using methods known in the art. Guidance for determining residues which may be altered while still maintaining activity can be found in the following references: Schorken et al. "Identification of catalytically important residues in the active site of *Escherichia coli* transaldolase" *Eur. J. Biochem* 268:2408-2415 (2001); and Schorken et al. "Disruption of *Escherichia coli* transaldolase into catalytically active monomers: evidence against half-of-the-sites mechanism" *FEBS Lett.* 441:247-150 (1998).

To evaluate the degree of homology, known calculation methods can be used, such as BLAST search, FASTA search and CrustalW. BLAST (Basic Local Alignment Search Tool) is the heuristic search algorithm employed by the programs blastp, blastn, blastx, megablast, tblastn, and tblastx; these programs ascribe significance to their findings using the statistical methods of Karlin, Samuel and Stephen F. Altschul ("Methods for assessing the statistical significance of molecular sequence features by using general scoring schemes". Proc. Natl. Acad. Sci. USA, 1990, 87:2264-68; "Applications and statistics for multiple high-scoring segments in molecular sequences". Proc. Natl. Acad. Sci. USA, 1993, 90:5873-7). FASTA search method is described by W. R. Pearson ("Rapid and Sensitive Sequence Comparison with FASTP and FASTA", Methods in Enzymology, 1990 183:63-98). ClustalW method is described by Thompson J. D., Higgins D. G. and Gibson T. J. ("CLUSTAL W: improving the sensitivity of progressive multiple sequence alignment through sequence weighting, position-specific gap penalties and weight matrix choice", Nucleic Acids Res. 1994, 22:4673-4680).

Changes to transaldolase such as those described above are typically conservative changes so as to maintain transaldolase activity. Substitution changes include those in which at least one residue in the amino acid sequence has been removed and a different residue inserted in its place. Examples of amino acids which may be substituted for an original amino acid in a transaldolase protein and which are regarded as conservative substitutions include: Ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln, lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

The DNA encoding substantially the same protein as the protein defined in (A) may be obtained by, for example, modification of nucleotide sequence encoding the protein defined in (A) using site-directed mutagenesis so that one or more amino acid residue will be deleted, substituted, inserted or added. Such modified DNA can be obtained by conventional methods using treatment with reagents and conditions generating mutations. Such treatment includes treatment the DNA encoding proteins of present invention with hydroxylamine or treatment the bacterium harboring the DNA with UV irradiation or reagent such as N-methyl-N'-nitro-N-nitrosoguanidine or nitrous acid.

The DNA encoding proteins of the present invention include variants which can be found in different strains of bacteria belonging to the genus *Escherichia* by virtue of natural diversity. DNA encoding such variants can be obtained by isolating the DNA which hybridizes to the talB gene or a part thereof under stringent conditions, and which encodes the protein having an activity of transaldolase. The term "stringent conditions" may include conditions under which a so-called specific hybrid is formed, and a non-specific hybrid is not formed. For example, stringent conditions includes conditions under which DNAs having high homology, for instance DNAs having homology not less than 70%, preferably not less than 80%, more preferably not less than 90%, most preferably not less than 95% to each other, are able to hybridize. Alternatively, stringent conditions may include conditions which are typical washing conditions for Southern hybridization, e.g., 60° C., 1×SSC 0.1% SDS, preferably 0.1×SSC, 0.1% SDS. As a probe for the DNA that codes for variants and hybridizes with talB gene, a partial sequence of the nucleotide sequence of SEQ ID NO: 1 can also be used. Such a probe may be prepared by PCR using oligonucleotides based on the nucleotide sequence of SEQ ID NO: 1 as primers, and a DNA fragment containing the nucleotide sequence of SEQ ID NO: 1 as a template. When a DNA fragment of about 300 bp in length is used as the probe, the washing conditions for the hybridization can be, for example, 50° C., 2×SSC, and 0.1% SDS.

Transformation of bacterium with a DNA encoding a protein means introduction of the DNA into a bacterium, for example, by conventional methods to increase the expression of the gene encoding the protein of present invention and to enhance the activity of the protein in the bacterium.

The bacterium of the present invention also includes one wherein the activity of the protein of the present invention is enhanced by transformation of said bacterium with DNA encoding a protein as defined in (A) or (B), or by alteration of an expression regulatory sequence of said DNA on the chromosome of the bacterium.

The DNA which is used for modification of the bacterium of the present invention may encode a protein having an activity of the transaldolase. More specifically, the DNA may be the talB gene. The talB gene can be obtained by, for example, PCR using primers based on the nucleotide sequence shown in SEQ ID No: 1.

The methods of the enhancement of gene expression include increasing the gene copy number. Introduction of a gene into a vector that is able to function in a bacterium belonging to the genus *Escherichia* increases the copy number of the gene. Multi-copy vectors are preferably used, and include pBR322, pUC19, pBluescript KS$^+$, pACYC177, pACYC184, pAYC32, pMW119, pET22b and the like. Enhancement of gene expression can be achieved by introducing multiple copies of the gene into a bacterial chromosome by, for example, homologous recombination methods and the like.

Alternatively, the enhancement of gene expression can be achieved by placing the DNA of the present invention under the control of more potent promoter rather than the native promoter. Strength of a promoter is defined by frequency of acts of the RNA synthesis initiation. Methods for evaluation the strength of promoter and an examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5, 2987-2994). For example, the P$_R$ promoter is known to be a potent constitutive promoter. Other known potent promoters are the P$_L$ promoter, lac promoter, trp promoter, trc promoter, of lambda phage and the like.

Enhancing translation can be achieved by introducing a more efficient Shine-Dalgarno sequence in place of the native SD sequence into the DNA of the present invention. The SD sequence is a region upstream of the start codon of mRNA which interacts with the 16S RNA of ribosome (Shine J. and Dalgarno L., Proc. Natl. Acad. Sci. USA, 1974, 71, 4, 1342-6).

Use of potent promoters can be combined with multiplication of gene copies.

Methods for preparation of chromosomal DNA, hybridization, PCR, preparation of plasmid DNA, digestion and ligation of DNA, transformation, selection of an oligonucleotide as a primer and the like include typical methods well known to one of ordinary skill in the art. Such methods are described in Sambrook, J., and Russell D., "Molecular Cloning A Laboratory Manual, Third Edition", Cold Spring Harbor Laboratory Press (2001) and the like.

The bacterium of the present invention can be obtained by introduction of the aforementioned DNAs into a bacterium which inherently has the ability to produce L-histidine. Alternatively, the bacterium of present invention can be obtained by imparting the ability to produce L-histidine to the bacterium already harboring the DNAs.

As a parent strain which is to be enhanced in activity of the protein of the present invention, bacteria belonging to the genus *Escherichia* having L-histidine-producing ability, the L-histidine-producing bacterium strains belonging to the genus *Escherichia,* such as *E. coli* strain 24 (VKPM B-5945, Russian patent 2003677); *E. coli* strain 80 (VKPM B-7270, Russian patent 2119536); *E. coli* strains NRRL B-12116-B12121 (U.S. Pat. No. 4,388,405); *E. coli* strains H-9342 (FERM BP-6675) and H-9343 (FERM BP-6676) (U.S. Pat. No. 6,344,347); *E. coli* strain H-9341 (FERM BP-6674) (European patent application 1085087A2); *E. coli* strain AI80/pFM201 (U.S. Pat. No. 6,258,554) and the like are encompassed.

It is desired that the L-histidine-producing bacterium be further modified to have enhanced expression of L-histidine biosynthesis genes. Genes effective for L-histidine biosynthesis include the hisG gene and genes of the hisBHAFI operon. The hisG gene encoding an ATP phosphoribosyl transferase of which feedback inhibition by L-histidine is desensitized (Russian patents 2003677 and 2119536) is preferred.

The method of present invention includes production of L-histidine comprising the steps of cultivating the bacterium of the present invention in a culture medium, allowing the L-histidine to be produced, and collecting the accumulated L-histidine from the culture medium.

In the present invention, the cultivation, collection and purification of L-histidine from the medium and the like may be performed by conventional fermentation methods for production of an amino acid using a microorganism.

A medium used for culture may be either a synthetic medium or a natural medium, so long as the medium includes a carbon source and a nitrogen source and minerals and, if necessary, appropriate amounts of nutrients which the microorganism requires for growth.

The carbon source may include various carbohydrates such as glucose and sucrose, and various organic acids. Depending on the mode of assimilation of the used microorganism, alcohol including ethanol and glycerol may be used.

As the nitrogen source, various ammonium salts such as ammonia and ammonium sulfate, other nitrogen compounds such as amines, a natural nitrogen source such as peptone, soybean-hydrolysate and digested fermentative microorganism are used.

As minerals, potassium monophosphate, magnesium sulfate, sodium chloride, ferrous sulfate, manganese sulfate, calcium chloride, and the like are used. Some additional nutrient can be added to the medium if necessary. For instance, if the microorganism requires proline for growth (proline auxotrophy) the sufficient amount of proline can be added to the medium for cultivation.

The cultivation is performed preferably under aerobic conditions such as a shaking culture, and stirring culture with aeration, at a temperature of 20 to 42° C., preferably 37 to 40° C. The pH of the culture is usually between 5 and 9, preferably between 6.5 and 7.2. The pH of the culture can be adjusted with ammonia, calcium carbonate, various acids, various bases, and buffers. Usually, an 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by ion-exchange, concentration and crystallization methods.

EXAMPLES

The present invention will be more concretely explained with reference to the following Examples. In the Examples, an amino acid is of L-configuration unless otherwise noted.

Example 1

Cloning the talB gene from *E. coli*

The entire nucleotide sequence of *E. coli* strain K-12 has been reported (Science, 277, 1453-1474, 1997). Based on the reported nucleotide sequence, the primers depicted in SEQ ID No. 3 (primer 1) and No. 4 (primer 2) were synthesized. Primer 1 is a sequence from 74 to 54 bp upstream of the start codon of talB gene with the restriction enzyme BglII recognition site introduced at the 5' thereof. Primer 2 is a sequence complementary to a sequence from 82 to 104 bp downstream of the termination codon of talB gene with the restriction enzyme XbaI recognition site introduced at the 5'-end thereof.

The chromosomal DNA of *E. coli* K12 which was used as template for PCR was prepared by an ordinary method. PCR was carried out on GENEAMP PCR System 2400 (Applied Biosystems), a PCR amplification system, under the following conditions: initial DNA denaturation at 95° C. for 5 min; then 30 cycles of denaturation at 95° C. for 30 sec, annealing at 56° C. for 60 sec and elongation at 72° C. for 120 sec; the final polymerization for 7 min. at 72° C. using Taq polymerase (Fermentas, Lithuania). The obtained PCR fragment containing the talB gene without a promoter was treated with BglII and XbaI and inserted under the control of the $P_R$ promoter in the pMW119-$P_R$ vector which had been previously treated with the same enzymes. Vector pMW119-$P_R$ was constructed from commercially available vector pMW119 by insertion of $P_R$ promoter from phageλ. Thus plasmid pMW-$P_R$-talB was obtained.

Example 2

Effect of Enhanced Expression of talB Gene on Histidine Production

The histidine-producing *E. coli* strain 80 was used as the parental strain for transformation with plasmid PMW-$P_R$-talB. The strain 80 has been described in Russian patent 2119536 and deposited in the Russian National Collection of Industrial Microorganisms (Russia, 113545 Moscow, $1^{st}$ Dorozhny proezd, 1) on Oct. 15, 1999 under accession number VKPM B-7270. It was converted to an international deposit under the provisions of the Budapest Treaty on Jul. 12, 2004.

Both strains 80 and 80/PMW-$P_R$-talB were cultivated in L broth with 1 g/l of streptomycin for 6 hours at 29° C. Then, 0.1 ml of obtained culture was inoculated into 2 ml of fermentation medium in 20×200 mm test tube and cultivated for 65 hours at 29° C. with a rotary shaker (350 rpm). After the cultivation the amount of histidine which had accumulated in the medium was determined by paper chromatography. The paper was developed with a mobile phase:

n-butanol:acetic acid:water=4:1:1 (v/v). A solution of ninhydrin (0.5%) in acetone was used as a visualizing reagent.

The composition of the fermentation medium (pH 6.0) (g/l):

| | |
|---|---|
| Glucose | 100.0 |
| Mameno (soybean protein hydrolysate) | 0.2 of TN |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |
| Streptomycin | 1.0 |

Obtained data are presented in the Table 1.

TABLE 1

| E. coli strain | $OD_{450}$ | Amount of histidine, g/l |
|---|---|---|
| 80 (VKPM B-7270) | 27.5 | 16.2 |
| 80/pMW-P$_R$-talB | 28.2 | 19.1 |

It can be seen from the Table 1 that enhanced expression of talB gene improved histidine production by the E. coli strain 80.

We claim:

1. An L-histidine-producing bacterium of the *Enterobacteriaceae* family, wherein the bacterium has been modified to enhance transaldolase activity by increasing the copy number of the transaldolase gene or by replacing a promoter sequence of the transaldolase gene with a stronger promoter sequence, wherein said transaldoase gene comprises a DNA which is 90% or more homologous to nucleotides 1-954 of SEQ ID No. 1 and encodes a protein which has transaldolase activity, and wherein said bacterium has been further modified to have enhanced expression of an L-histidine biosynthetic gene.

2. The bacterium according to claim 1, wherein said bacterium belongs to the genus *Escherichia*.

3. The bacterium according to claim 1, wherein said copy number is increased by transformation of said bacterium with a multi-copy vector harboring said transaldolase gene.

4. The bacterium according to claim 2, wherein said transaldolase gene is derived from a bacterium belonging to the genus *Escherichia*.

5. The bacterium according to claim 1, wherein said transaldolase gene encodes a protein selected from the group consisting of:
   (A) a protein comprising the amino acid sequence shown in SEQ ID NO: 2; and
   (B) a protein comprising an amino acid sequence which includes deletions, substitutions, insertions or additions of one to 30 amino acids in the amino acid sequence shown in SEQ ID NO: 2, and which has transaldolase activity.

6. The bacterium according to claim 1, wherein said transaldolase gene is selected from the group consisting of:
   (a) a DNA comprising a nucleotide sequence of nucleotides 1 to 954 in SEQ ID NO: 1;
   (b) a DNA which is hybridizable with a nucleotide sequence of nucleotides 1-954 in SEQ ID NO: 1 under stringent conditions and codes for a protein having transaldolase activity; and
   (c) a DNA which is hybridizable with a probe which can be prepared from the nucleotide sequence of nucleotides 1-954 in SEQ ID NO: 1 under stringent conditions and codes for a protein having transaldolase activity,
   wherein said stringent conditions comprise washing at 60° C. and at a salt concentration of 1×SSC and 0.1% SDS.

7. The L-histidine-producing bacterium of the Enterobacteriaceae family of claim 1, wherein said transaldolase gene encodes a protein selected from the group consisting of
   a) a protein comprising the amino acid sequence of SEQ ID NO. 2, and
   b) a protein which has 95% or more homology to the amino acid sequence of SEQ ID NO. 2 and has transaldolase activity.

8. The L-histidine-producing bacterium of the Enterobacteriaceae family of claim 1, wherein said transaldolase gene is a nucleotide sequence selected from the group consisting of:
   (a) a DNA comprising a nucleotide sequence of nucleotides 1 to 954 in SEQ ID NO: 1; and
   (b) a DNA which is hybridizable with a nucleotide sequence of nucleotides 1-954 in SEQ ID NO: 1 under stringent conditions and has 95% or more homology to nucleotides 1-954 of SEQ ID NO. 1, and encodes a protein having transaldolase activity, wherein said stringent conditions comprise washing at 60° C. and at a salt concentration of 1×SSC and 0.1% SDS.

9. The bacterium according to claim 1, wherein said L-histidine biosynthetic gene is the ATP phosphoribosyl transferase gene from an *Escherichia* bacteria.

10. The bacterium according to claim 9, wherein said ATP phosphoribosyl transferase gene is desensitized to feedback inhibition by L-histidine.

11. The bacterium according to claim 7, wherein said L-histidine biosynthetic gene is the ATP phosphoribosyl transferase gene from an *Escherichia* bacteria.

12. The bacterium according to claim 11, wherein said ATP phosphoribosyl transferase gene is desensitized to feedback inhibition by L-histidine.

13. The bacterium according to claim 8, wherein said L-histidine biosynthetic gene is the ATP phosphoribosyl transferase gene from an *Escherichia* bacteria.

14. The bacterium according to claim 13, wherein said ATP phosphoribosyl transferase gene is desensitized to feedback inhibition by L-histidine.

* * * * *